United States Patent [19]

Fuchs et al.

[11] Patent Number: 5,071,435

[45] Date of Patent: Dec. 10, 1991

[54] EXTENDIBLE BONE PROSTHESIS

[76] Inventors: Albert Fuchs, 1508 Centinela Ave., Apt. 6, Los Angeles, Calif. 90025; Kenneth M. Drobish, 2917 Jane Ct., Newbury Park, Calif. 91320-4425

[21] Appl. No.: 630,543

[22] Filed: Dec. 20, 1990

[51] Int. Cl.[5] ................................................ A61F 1/00
[52] U.S. Cl. ...................................... 623/16; 623/18; 623/22; 623/38
[58] Field of Search ...................... 623/16, 18, 22, 23, 623/38, 44; 606/63

[56] References Cited

U.S. PATENT DOCUMENTS 4,157,715  6/1979  Westerhoff ........................... 606/63
4,892,546  1/1990  Kotz et al. ............................ 623/18

OTHER PUBLICATIONS

"A Growth-Imitating Lengthening Element for Modular Femoral Endoprostheses", van Krieken et al., Bristol-Meyers Orthopedic Symposium 1985.
"Design & Clinical Use of Extending Prosthesis", Scales et al., Bristol-Myers Orthopaedic Symposium, 1985.
"Extendible Prosthesis: An Alternative to Amputation", Lewis et al., Bristol-Myers Orthopaedic Symposium, 1985.
"Biomechanical Evaluation of an Extending Adjustable Tumor Prosthesis", Spires et al., Bristol-Meyers Orthopaedic Symposium, 1985.

Primary Examiner—Randy Citrin Shay
Attorney, Agent, or Firm—Norton R. Townsley

[57] ABSTRACT

A bone prosthesis (10) which is hydraulically operated is disclosed. It comprises a cylinder (12), which is closed at one end, and piston (28), which slides inside the cylinder (12). The relative locations of the cylinder (12) and piston (28) are controlled by a liquid (26) filled bladder (24) which is located inside the cylinder (12). Liquid (26) is introduced into the bladder (24) via a valve (22) which fits through the side wall (21) of the cylinder (12). The valve (22) is constructed so that liquid (26) can be introduced to or removed from the bladder (24). One end of the prosthesis (10) is shaped to mate with the remaining segment of bone. The other end of the prosthesis (10) is shaped to replace the other end of the surgically removed bone segment. In addition, the internal surface (18) of the cylinder (12) and the external surface (30) of the piston (28) are grooved or keyed so as to prevent rotation of the piston (28) inside the cylinder (12). The entire prosthesis (10) is fabricated from bio-compatible materials. A method of surgically inserting and post-operatively lengthening this invention is also disclosed.

8 Claims, 4 Drawing Sheets

EXTENDIBLE BONE PROSTHESIS

BACKGROUND OF THE INVENTION

The present invention relates to the field of prostheses. More particularly it relates to the field of prostheses, used to replace surgically removed bone segments.

In the treatment of diseases it is sometimes necessary to remove and replace a segment of bone. Such is frequently the case in treatment of bone cancers. Replacement of the diseased segment with a prosthesis is preferable to amputation.

The state of medical art has developed to the point that, when the patient is fully grown, a fixed size prosthesis can be inserted to replace the removed bone segment. For example, hips, and segments of fibula, tibia, ulna, radius and humerus are commonly replaced in this way. However, when the patient is a child, an extendible prosthesis is necessary to maintain equality of limb length as the child grows.

Two types of extendible bone prostheses have been used in recent years. One type has an internal gear and worm mechanism. To lengthen this prosthesis requires turning the gear with a special key. The other type is extended by inserting ball bearings of a standard size into a telescoping shaft thus it can only be extended in quantum increments and cannot be shortened once extended. Both these prostheses require major invasive operations for lengthening and since the entire compressive load is supported by metal, they are susceptible to fatigue failures.

Other designs utilizing an electromotor with an inductive power supply and a rotating magnetic field have been proposed. The main difficulty with these proposals is the difficulty of producing enough force to extend the limb.

An extendible bone prosthesis that did not depend on a metal to support the compressive load and which did not require major invasive surgical techniques for operation would satisfy a long felt need in the field of pediatric orthopaedic surgery.

SUMMARY OF THE INVENTION

The present invention is a bone prosthesis which is hydraulically operated. It can be easily extended by any desired amount as the patient grows and can be shortened if necessary. Furthermore, it is not subject to fatigue failures and its length can be changed by non-major invasive techniques.

This invention comprises a cylinder, which is closed at one end, and a piston, which slides inside the cylinder. The relative locations of the cylinder and piston are controlled by a liquid filled bladder which is located inside the cylinder. Liquid is introduced into the bladder via a valve which fits through the side wall of the cylinder. The valve is constructed so that it will not leak and so that liquid can be added to or removed from the bladder. One end of the prosthesis is shaped to mate with the remaining segment of bone. The other end of the prosthesis is shaped to replace the other end of the surgically removed bone segment. In addition, the internal surface of the cylinder and the external surface of the piston are grooved or keyed so as to prevent rotation of the piston inside the cylinder. The entire prosthesis is fabricated from bio-compatible materials.

A method of surgically inserting and post-operatively lengthening this invention is also disclosed.

An appreciation of other aims and objectives of the present invention and a more complete and comprehensive understanding of this invention may be achieved by studying the following description of a preferred embodiment and by referring to the accompanying drawings.

DETAILED DESCRIPTION OF THE PREFERRED EMBODIMENT

Figure 1:
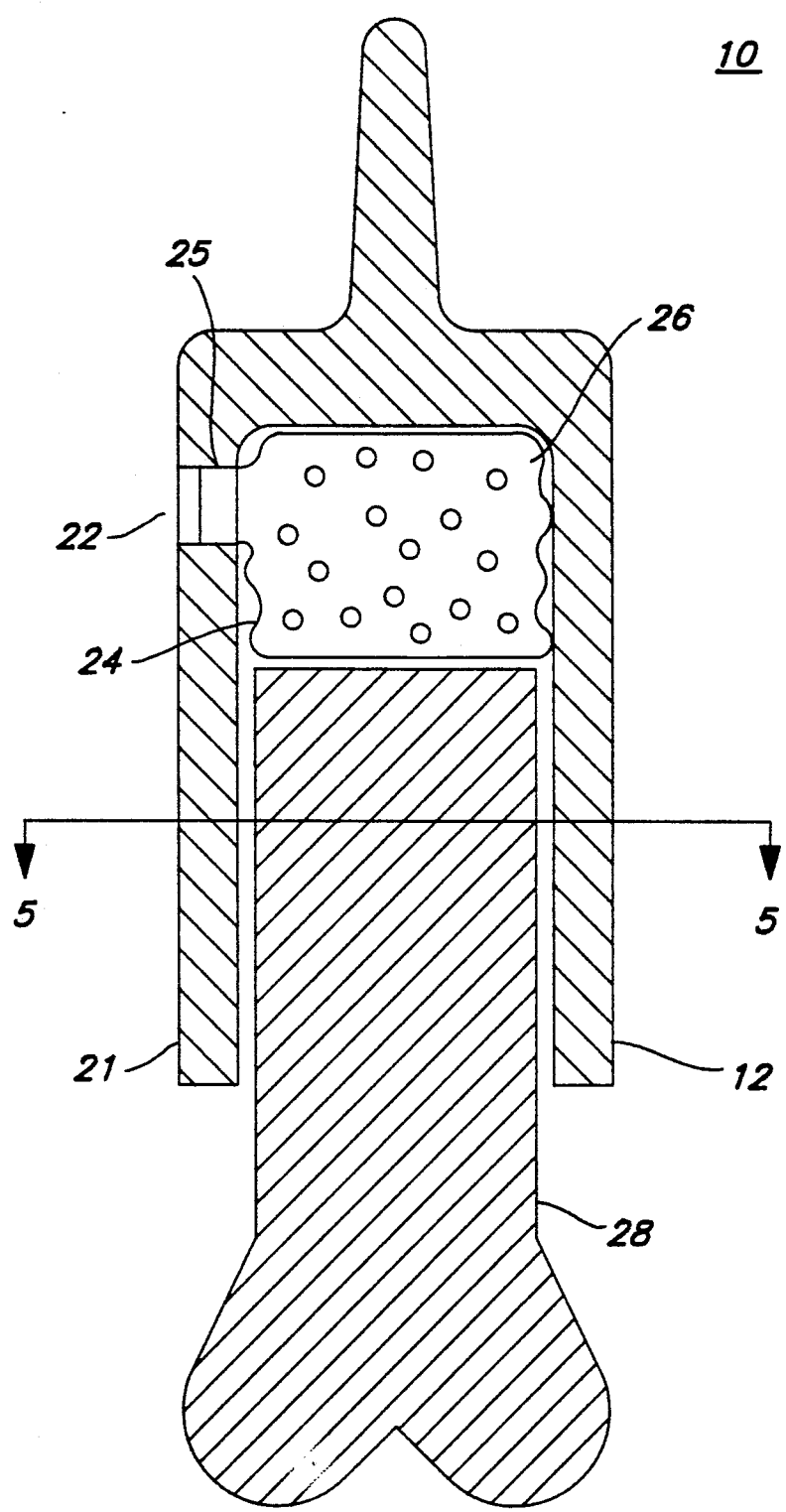
FIG. 1 is a longitudinal cross-section of a typical extendible bone prosthesis.

FIG. 1 shows the main components of a typical, completely assembled, extendible bone prosthesis 10. The figure shows how the piston 28 fits inside the cylinder 12. Controlling the location of the piston 28 inside the cylinder 12 is a bladder 24 which is filled with a liquid 26. A valve 22, fitted through the wall 21 of the cylinder 12 and attached to its neck 25 allows introduction of the liquid 26 into the bladder 24. The valve 22 is a check valve: that is it is constructed so that liquid 26 can be introduced to the bladder 24 but so that none can escape from the bladder 24. All components of the prosthesis 10 are made from bio-compatible materials. In the preferred embodiment the liquid is a saline solution or cerebrospinal fluid.

Figure 2:
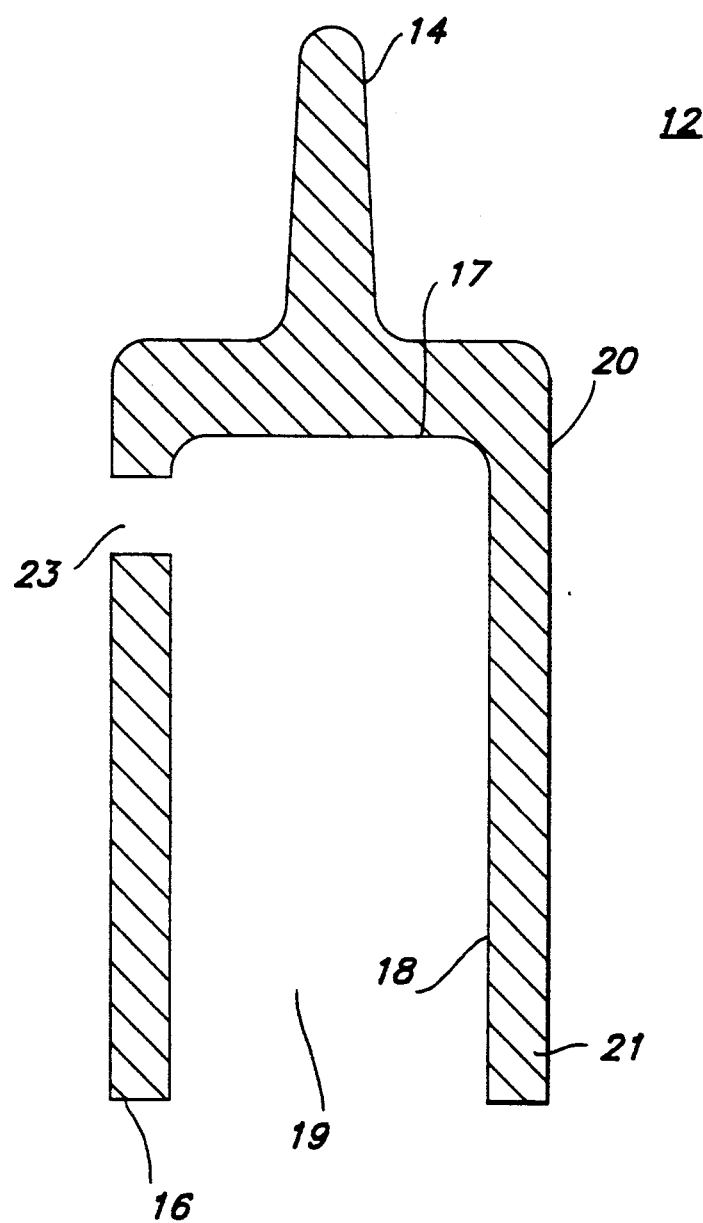
FIG. 2 is a longitudinal cross-section of a typical cylinder.

FIG. 2 clarifies the construction of the cylinder component 12. The cylinder 12 has a closed proximal end 14 and an open distal end 16. The cylinder 12 encloses a cavity 19 and has an internal proximal end 17, an inner surface 18, and an exterior surface 20. There is an opening 23 through the side wall 21 of the cylinder 12, adjacent to the internal proximal end 17.

The proximal end 14 shown in FIG. 2 is specially shaped to fit into the medullary cavity of a long bone. Persons possessing ordinary skill in the art to which this invention pertains will readily recognize that this end 14 could alternatively be shaped like an epiphysis in order to fit into a joint, such as a knee or an elbow. In the preferred embodiment, the cylinder 12 is made from stainless steel or titanium alloy.

Figure 3:
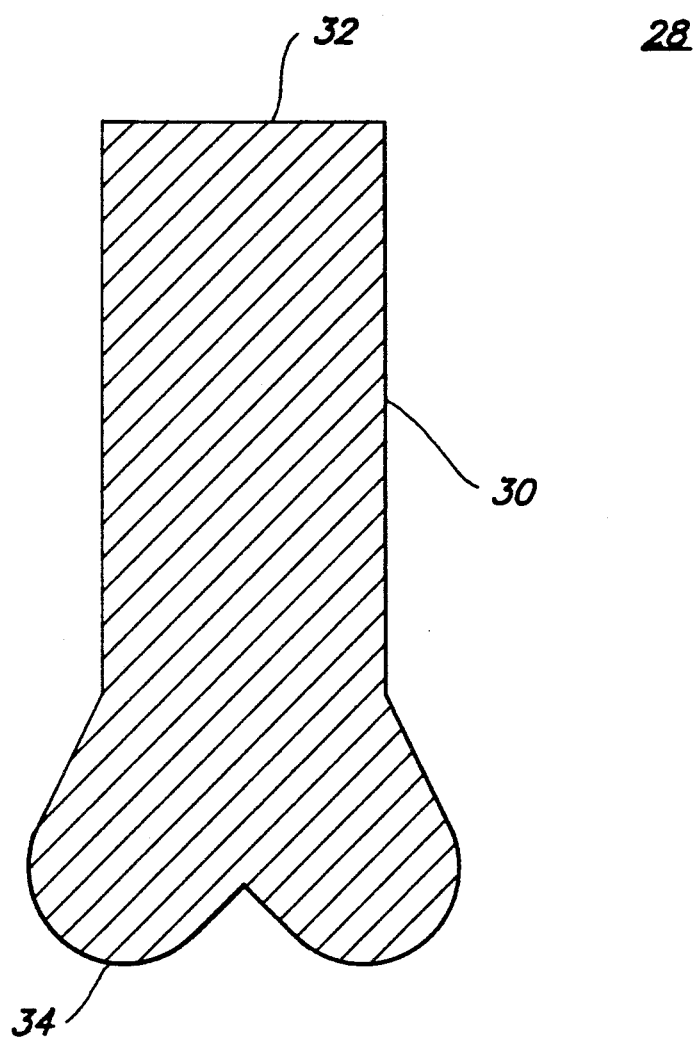
FIG. 3 is a longitudinal cross-section of a typical piston.

FIG. 3 shows the details of the piston 28. The piston 28 is solid and is cylindrical in shape. Being solid, it has an exterior surface 30, a proximal end 32 and a distal end 34. The proximal end 32, is sized to slide into the cavity 19 of the cylinder 12. The distal end 34 shown in FIG. 3 is shaped like an epiphysis in order to fit into a joint, such as a knee or an elbow. Persons possessing ordinary skill in the art to which this invention pertains will readily recognize that this end 34 could alternatively be shaped to fit into the medullary cavity of a long bone. In the preferred embodiment, the piston 28 is made from stainless steel or titanium alloy.

Figure 4:
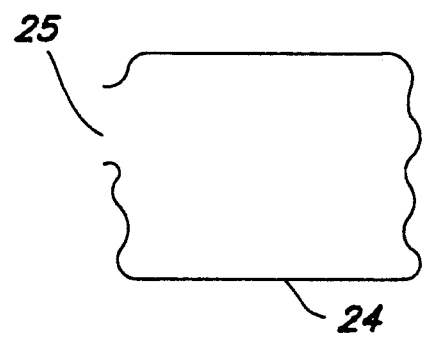
FIG. 4 is a cross-section of a typical bladder.

FIG. 4 is a cross-section of a typical bladder 24, showing that it is flaccid, so that its volume can be changed considerably, and it has a neck 25. In the preferred embodiment the bladder 24 is made from a polyurethane or silicone elastomer.

Figure 5:
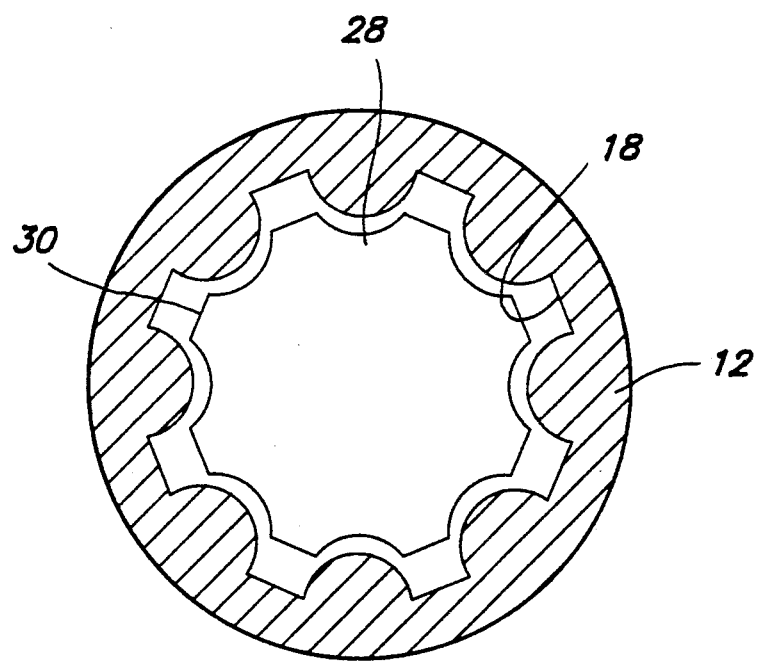
FIG. 5 is a transverse cross-section of the prosthesis of FIG. 1, at the location marked 5—5.

FIG. 5 demonstrates that the outer surface 30 of the piston 28 and the inner surface 18 of the cylinder 12 are grooved. This prevents rotation of the cylinder 12 and the piston 28 in relation to each other. While FIG. 5 shows that the surfaces 30 and 18 are grooved, persons possessing ordinary skill in the art to which this invention pertains will recognize that alternate methods, such as keyways slots, or non-circular cylinders could be devised to prevent rotation.

The assembled prosthesis 10 can be inserted in place of a diseased bone segment that has been surgically removed. The grooving of the surfaces 30 and 18 ensures that the epiphysial end of the prosthesis 10 does not rotate in the joint into which it fits. The prosthesis 10 is constructed so that at completion of the surgery, the valve 22 is covered by a minimum of tissue. At initial insertion, the bladder 24 contains a minimal quantity of liquid 26. The hydraulic pressure in the bladder is sufficient to support compressive forces on the limb.

Periodically, as the child grows, more liquid 26 is introduced into the bladder 24. In the preferred embodiment, the liquid 26 is introduced by injection, thus obviating the need for even minor surgery. When more liquid 26 is introduced, the volume in the bladder 24 increases. This increased volume causes an increase in separation between the piston 28 and the cylinder 12. This results in an overall lengthening of the prosthesis 10. The increase in length of the prosthesis 10 can be precisely controlled by the quantity of liquid 26 introduced. Thus the increase in length is infinitely variable.

A prosthesis made and operated in accordance with this invention has many advantages. Its metallic components do not support the entire compressive load and are thus not subject to fatigue failures. Its lengthening can be precisely controlled. And it can be lengthened by non-major invasive techniques.

Persons possessing ordinary skill in the art to which this invention pertains will appreciate that other modifications and enhancements may be made without departing from the spirit and scope of the claims that follow.

LIST OF REFERENCE NUMERALS

FIG. 1

10 Extendible bone prosthesis
12 Cylinder
21 Side wall
22 Valve
24 Bladder
25 Bladder neck
26 Liquid
28 Piston

FIG. 2

12 Cylinder
14 Proximal end of cylinder
16 Distal end of cylinder
17 Internal proximal end
18 Inner surface of cylinder
19 Cavity
20 Exterior surface of cylinder
21 Cylinder wall
23 Opening

FIG. 3

28 Piston
30 Exterior surface of piston
32 Proximal end of piston
34 Distal end of piston

FIG. 4

24 Bladder
25 Bladder neck

FIG. 5

12 Cylinder
18 Inner surface of cylinder
28 Piston
30 Exterior surface of piston

What is claimed is:

1. An apparatus comprising:
a cylinder means (12) for replacing a first end of a surgically removed bone segment; said cylinder means (12) having a proximal end (14), a distal end (16), an internal cylindrical surface (18), an external surface (20), an internal cavity (19) opening to said distal end (16), an internal end (17) and a side wall (21); said side wall having an opening (23) close to said proximal end (14), communicating with said internal cavity (19); said cylinder means (12) being made of a strong, lightweight, bio-compatible material;
a piston means (28) for replacing a second end of said surgically removed bone segment; said piston means (28) having a proximal end (32), a distal end (34) and an exterior surface (30); said proximal end (32) of said piston means (28) being slidably disposed inside said cylindrical cavity (19) of said cylinder means (12); said piston means (12) being made of a strong, lightweight, bio-compatible material;
a bladder means (24) for controlling the location of said piston means (28) within said internal cavity (19) of said cylinder means (12); said bladder means (24) being located inside said internal cavity (19) of said cylinder means (12) and between said internal end (17) of said cylinder means (12) and said proximal end (32) of said piston (28); said bladder means (24) having a neck (25); said neck (25) being attached to said opening (23) in said side wall (21) of said cylinder means (12); said bladder means being made of a flexible, biocompatible material;
a liquid means (26) for controlling the volume of said bladder means (24); said liquid means (26) being contained within said bladder means (24); said liquid means (26) being bio-compatible; and
a valve means (22) for controlling introduction of said liquid means (26) into and removal of said liquid means (26) from said bladder means (24); said valve means being fastened to said neck (25) of said bladder (24); said valve means being made of a bio-compatible material;
said internal surface (18) of said cylinder means (12) and said external surface (30) of said piston means (28) being formed to so as to prevent rotation of said piston means (28) inside said cylinder means (12).

2. The apparatus as claimed in Claim 1, in which said strong, lightweight bio-compatible material is selected from the group consisting of stainless steel and titanium alloy.

3. The apparatus as claimed in Claim 1, in which said flexible, bio-compatible material is selected from the group consisting of polyurethane elastomer and silicone elastomer.

4. The apparatus as claimed in Claim 1, in which said liquid means is selected from the group consisting of saline solution and cerebrospinal fluid.

5. An extendible bone prosthesis comprising:
a cylinder (12) having a proximal end (14), a distal end (16), an internal cylindrical surface (18), an external surface (20), an internal cavity (19) opening to said distal end (16), an internal end (17) and a side wall (21); said side wall having an opening (23) close to said proximal end (14), communicating with said internal cavity (19); said cylinder (12) being made of a strong, lightweight, bio-compatible material;
a piston (28) having a proximal end (32), a distal end (34) and an exterior surface (30); said proximal end (32) of said piston (28) being slidably disposed inside said cylindrical cavity (19) of said cylinder (12); said piston (12) being made of said strong, lightweight, bio-compatible material;
a bladder (24), located inside said internal cavity (19) of said cylinder means (12) and between said internal end (17) of said cylinder means (12) and said proximal end (32) of said piston (28); said bladder (24) having a neck (25); said neck (25) being attached to said opening (23) in said side wall (21) of said cylinder (12); said bladder being made of a flexible, bio-compatible material;
a bio-compatible liquid (26) contained within said bladder (24); and
a valve (22) fastened to said neck (25) of said bladder (24); said valve (22) controlling introduction of said bio-compatible liquid (26) into and removal of said bio-compatible liquid (26) from said bladder (24); said valve (22) being made of a bio-compatible material;
said internal surface (18) of said cylinder (12) and said external surface (30) of said piston (28) being formed to so as to prevent rotation of said piston (28) inside said cylinder (12).

6. The extendible bone prosthesis as claimed in claim 5, in which said strong, lightweight bio-compatible material is selected from the group consisting of stainless steel and titanium alloy.

7. The extendible bone prosthesis as claimed in claim 5, in which said flexible, bio-compatible material is selected from the group consisting of polyurethane elastomer and silicone elastomer.

8. The extendible bone prosthesis as claimed in claim 5, in which said bio-compatible liquid is selected from the group consisting of saline solution and cerebrospinal fluid.

* * * * *